US00PP10244P

United States Patent [19]

Egger

[11] Patent Number: Plant 10,244

[45] Date of Patent: Feb. 17, 1998

[54] ASIATIC HYBRID LILY PLANT NAMED 'BAL WHITE'

[75] Inventor: Donald L. Egger, Wilsonville, Oreg.

[73] Assignee: Cebeco Lilies, Inc., Aurora, Oreg.

[21] Appl. No.: 692,229

[22] Filed: Aug. 7, 1996

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Klarquist Sparkman Campbell Leigh & Whinston, LLP

[57] ABSTRACT

A new and distinct Asiatic lily hybrid having numerous white flowers, white buds, and strong stems with good foliage quality excellent for cut flowers.

1 Drawing Sheet

BACKGROUND OF THE INVENTION

The present invention relates to a new and distinct cultivar of Lily hybrid referred to commercially as an upright flowering Asiatic hybrid lily and given the cultivar name 'Bal White'. This invention was developed by controlled breeding in Aurora, Ore., using 'Mont Blanc' as the seed parent, and A-165-80, a proprietary, non-released plant, as the pollen parent.

This invention has not been observed under all possible environmental conditions. The phenotype may vary significantly with variations in environment such as temperature, light intensity, and day length, without, however, any variation in genotype.

The following traits have been repeatedly observed and are determined to be the basic characteristics of this invention which in combination distinguish this lily as a new and distinct cultivar: 1) white, medium size flowers with bright orange pollen; 2) beautiful white buds: 3) high bud count; 4) long lasting flowers; 5) strong stems with good quality foliage; 6) good vase life; and 7) early flowering. Bulbs of this plant may be precooled and forced out of season for uniform cut flower production. In addition, this new lily shows good disase resistance.

Compared to 'Sancerre' this invention has higher bud count, more virus resistance, stronger stems, and better vase life.

Asexual reproduction of this new variety has been accomplished at Cebeco Lilies, Inc., in Aurora, Ore., by scaling and tissue culture. The resulting plants have shown that the above-mentioned unique features are stable and reproduce true to type in each successive propagation.

Figure 2:
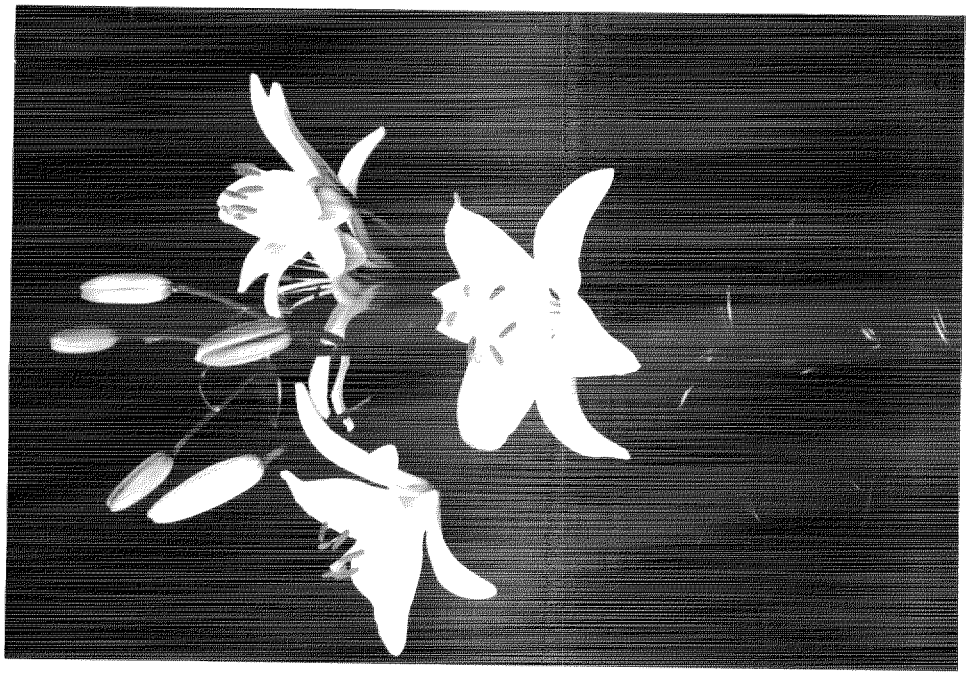
FIG. 2 is a photograph showing the 'Bal White' lily.
Figure 1:
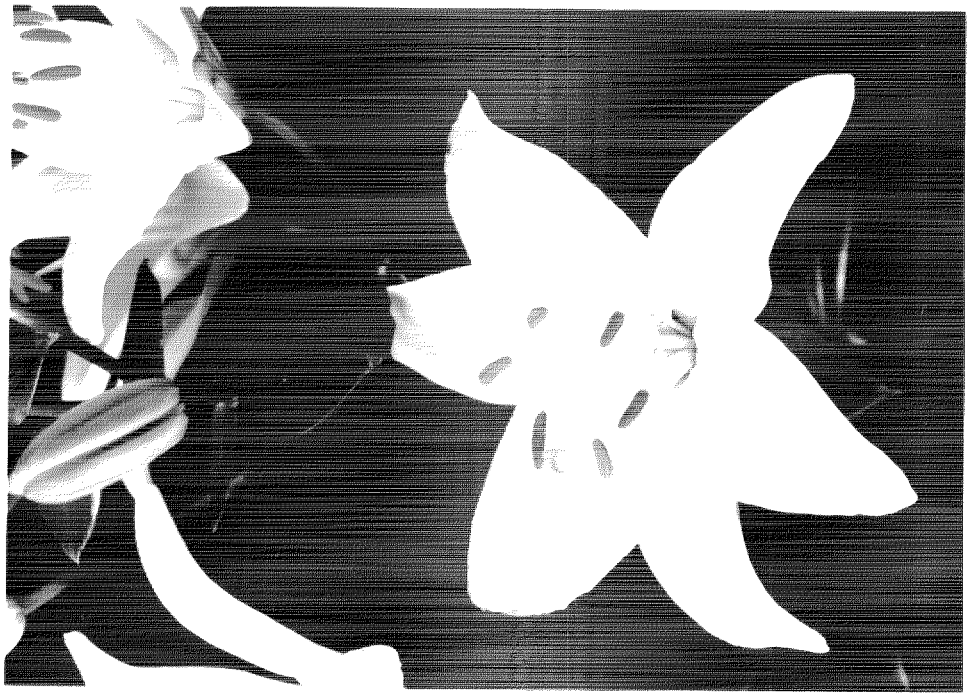
FIG. 1 is a close-up photograph which illustrates in greater detail a single flower of the new plant.

The photographs of the drawing were taken in June 1995 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouse in Aurora, Ore. in June 1995. Color references are made to The Royal Horticultural Society Colour Chart, except where the context indicates a term having its ordinary dictionary meaning.

The Plant

Origin: Seedling.

Parentage:

*Seed parent.*—'Mont Blanc'.

*Pollen parent.*—A-165-80

Commercial classification: Hybrid Asiatic Lily, cut flower type.

Classification: Division I-A, Upright Asiatic Hybrid Lily, according to the Horticultural Classification of Lilies by The Royal Horticultural Society of London.

Form: Single erect stem bearing terminal cluster of flowers.

Height: About 93 cm. from the top of the soil to the top of the flowers from bulbs of 12–14 cm. in circumference.

Stem color: Yellow green.

Growth habit: Vigorous, upright and rigid.

Internodes: About 3–15 mm.

Foliage:

*Arrangement.*—Spiral.

*Leaf size.*—To about 124 mm. long and 14 mm wide.

*Leaf shape.*—Lanceolate.

*Texture.*—Leathery.

*Aspect.*—Glossy.

*Color.*—Medium green on both sides. Closest to Yellow Green Group 147A.

Bulbs:

*Size.*—Variable, ranging to about 12–14 cm. in circumference as used commercially.

*Color.*—White.

The Bud

Size: About 63 mm. long and 21 mm. wide just prior to opening.

Shape: Ovoid with an obtuse tip.

Rate of opening: The mature bud opens slowly in response to light.

Color: Cream (Yellow Group 4D) with yellow green at apex.

The Flower

Blooming habit: Annually, once and early season.

Days to bloom: Flowers approximately 77 days after spring greenhouse planting under typical commercial flower forcing conditions of 15 degrees Celsius night time temperatures.

Inflorescence size: About 28 cm. high and 26 cm. wide when there are eleven flowers present.

Flower size: Medium-large.
*Diameter.*—About 14 cm.
*Depth.*—About 4 cm.
Borne: In a raceme of 11 flowers from bulbs 12–14 cm. in circumference.
Shape: When the flower first opens it is bowl shaped. Later, the shape flattens out and the tepals reflex slightly at the tips.
Tepalage:
*Number.*—Six.
*Arrangement.*—Imbricated.
*Shape.*—Ovate.
*Texture.*—Spongy, waxy.
*Aspect.*—Satiny.
*Size.*—Length: About 74 mm. Width: Inner tepals — about 41 mm. Outer tepals — about 33 mm.
Depth of imbrication: About 10 mm.
Nectary: About 2 cm. long; yellow white (8C) to yellow green (144B); glandular pubescent; channels together.
Projections: None.
Spots: Small and very few (0–5) on the inner tepals. Greyed-Purple Group 187C.
Blush: Slight, above the nectary, light yellow, Yellow Group 8C. Younger flowers have slightly more blush.
Color:
*Topside.*—White. Yellow White Group 158A with blush as described above.
*Bottomside.*—Yellow White Group 158A.
Discoloration: A shade lighter with age.
Fragrance: None.
Pedicle:
*Length.*—About 8–10 cm.
*Color.*—Yellow green 144A.
*Orientation.*—Ascending upwardly in a curve at about 45° from the horizontal.

The Reproductive Organs

Stamens:
*Number.*—Six, typical of the genus Lilium.
*Anthers before dehiscence.*—Size: About 17 mm. Color: Yellow Orange 22A.
*Filaments.*—Length: About 5 cm. Color: White. Yellow-White Group 158D on top half and White 155D on bottom.
Pollen:
*Color.*—Orange. Orange Group 24A.
Pistil:
*Number.*—One.
*Style.*—Length: About 44 mm. Color: White. Yellow-White Group 158A.
*Stigma.*—Color: Lightly stippled Greyed-Red Group 182C.

The Fruit

Fertility: Fertile.
Shape: Ovoid.
Color at maturity: Soft Brown.

I claim:

1. A new and distinct cultivar of Asiatic hybrid lily plant substantially as herein shown and described.

* * * * *